United States Patent [19]

Yurkewych et al.

[11] Patent Number: 5,061,244

[45] Date of Patent: Oct. 29, 1991

[54] PUDENDAL/PARACERVICAL BLOCK NEEDLE ASSEMBLY

[75] Inventors: George J. Yurkewych, Parsippany; Joseph J. Gregg, Hasbrouck Heights; Samuel D. Beley, Saddle Brook, all of N.J.

[73] Assignee: Becton, Dickinson and Company, Franklin Lakes, N.J.

[21] Appl. No.: 491,405

[22] Filed: Mar. 9, 1990

[51] Int. Cl.$^5$ ............................................. A61M 5/178
[52] U.S. Cl. ..................................... 604/164; 604/117
[58] Field of Search .............. 604/164, 165, 187, 198, 604/117, 280, 283, 158; 128/753, 754

[56] References Cited

U.S. PATENT DOCUMENTS

| | | |
|---|---|---|
| 2,700,385 | 1/1955 | Ortiz . |
| 2,712,314 | 7/1955 | Kohl . |
| 2,880,724 | 4/1959 | Velarde . |
| 3,356,089 | 12/1967 | Francis ................................ 604/117 |
| 3,380,448 | 4/1968 | Sadove et al. . |
| 3,995,629 | 12/1976 | Patel . |
| 4,275,728 | 6/1981 | Merry . |
| 4,710,171 | 12/1987 | Rosenberg ........................... 604/117 |
| 4,763,667 | 8/1988 | Manzo .............................. 604/164 X |
| 4,919,653 | 4/1990 | Martinez et al. .................... 604/117 |
| 4,973,313 | 11/1990 | Katsaros et al. ..................... 604/165 |

Primary Examiner—John D. Yasko
Attorney, Agent, or Firm—John L. Voellmicke

[57] ABSTRACT

A pudendal/paracervical block anesthesia needle assembly is provided. The assembly includes a needle guide which limits the extent to which a needle may be inserted within a patient. The needle guide includes a housing to which a cannula is secured. A needle assembly including a needle hub and needle are insertable within the guide such that the needle is positioned within the cannula and the needle hub within the guide housing. The needle guide housing includes a recess including two pairs of parallel walls. A pair of abutments, one positioned distal to the other, extend within the recess. The needle hub includes a contact surface which contacts one of the two abutments depending upon its rotational position. The extent to which the needle projects outside the cannula is determined by which abutment is engaged by the contact surface of the hub.

27 Claims, 4 Drawing Sheets

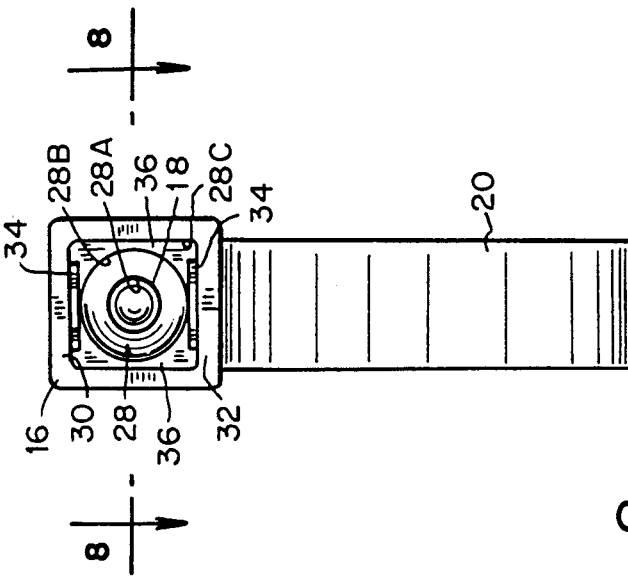
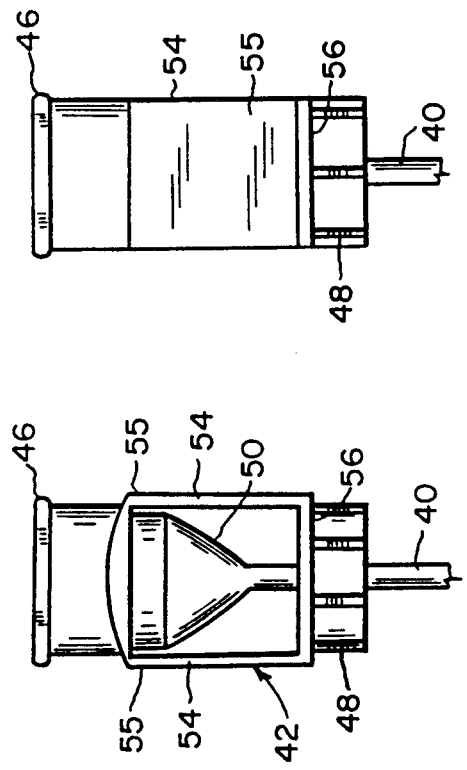
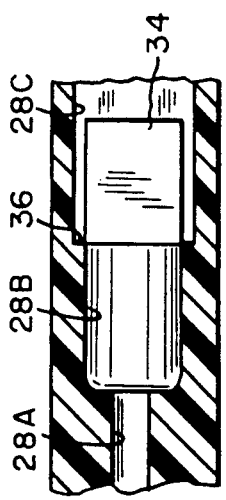
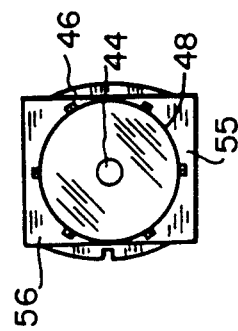

PUDENDAL/PARACERVICAL BLOCK NEEDLE ASSEMBLY

BACKGROUND OF THE INVENTION

1. Field of the Invention.

The field of the invention relates to needle assemblies for performing anesthesia procedures, particularly during childbirth.

2. Brief Description of the Prior Art.

Various instruments have been devised for providing local anesthetic during childbirth. During the first stage of labor, pain caused by dilation of the cervix may be relieved by a paracervical block. Pain at the time of delivery may be relieved with a transvaginal pudendal block.

In order to prevent accidental lacerations or punctures, pudendal/paracervical block anesthesia needle assemblies generally include a needle guide which is properly positioned within the patient prior to pushing the needle therethrough. It is also important to control the depth of needle penetration, and the needle guide should include means for limiting such penetration to less than a predetermined depth, such as about fifteen millimeters.

U.S. Pat. Nos. 2,700,385; 2,712,314; 2,880,724; 3,380,448; 3,995,629 and 4,275,728 disclose various instruments for performing pudendal/paracervical blocks or for administering other medicaments. The latter two patents disclose means for controlling the extent to which the needle tip will project from the needle guide. Specifically, the instruments disclosed in U.S. Pat. Nos. 3,995,629 and 4,275,728 allow the needle to be maintained in three positions: a retracted position, and two different extended positions to permit two different injection depths.

Another well known instrument for providing pudendal and/or paracervical blocks includes a needle guide comprising a handle, an elongate, open-ended tube secured to the handle, and an enlarged patient contacting tip member secured to the distal end of the tube. A needle having a hub on one end may be inserted through the tube until the hub contacts the proximal end of the tube. The needle is longer than the tube and, accordingly, the needle tip will protrude through the enlarged tip member. If the physician wishes to expose less of the needle tip, he or she must remove the needle from the tube and slip a separate movable needle collar over the needle and then re-insert the needle into the tube. This procedure is undesirable because it could result in needle point damage and/or accidental needle sticks. The needle collar engages the proximal end of the tube instead of the hub when the needle is inserted so that less of the needle protrudes through the enlarged tip member.

SUMMARY OF THE INVENTION

It is an object of the invention to provide an instrument for administering medicaments to a patient in a safe manner.

It is another object of the invention to provide an instrument including means for controlling the depth of a needle injection.

A still further object of the invention is to provide an instrument which prevents a needle from rotating while in use.

In accordance with these and other objects of the invention, an assembly is provided which is particularly well adapted for performing pudendal and paracervical blocks. The assembly includes a needle guide assembly and a needle assembly used in conjunction therewith. The needle guide assembly includes a housing having a recess defined in one end thereof. An abutment is provided within the recess for engaging the hub of the needle assembly, thereby preventing the needle from being injected beyond a selected depth. The needle assembly includes a needle secured to a needle hub. The needle hub is configured such that it engages the abutment when inserted within the recess while in a first rotational position, but avoids the abutment when inserted in a second rotational position. The needle may be injected to a greater depth when the hub avoids engagement with the abutment.

A second abutment may be provided for limiting the extent to which the hub may be inserted within the recess. The second abutment may also extend within the recess, and is preferably distal to the first-mentioned abutment.

To prevent the needle assembly from rotating, the recess and the needle hub may both have parallelpipedic configurations. The recess may have a substantially square cross sectional configuration while the hub is, at least in part, substantially rectangular in cross section.

A handle and guide cannula are secured to the housing, the guide cannula being in fluid communication with the recess. The handle preferably includes an oblong opening to facilitate insertion of a physician's thumb.

BRIEF DESCRIPTION OF THE DRAWINGS

FIG. 4 is an enlarged side elevation view of a needle hub employed in accordance with the invention;

FIG. 5 is an enlarged side elevation view of said needle hub rotated ninety degrees from the position shown in FIG. 4;

FIG. 6 is an end view of the needle guide assembly;

FIG. 7 is an enlarged end view of the needle assembly; and

FIG. 8 is a partial cross-sectional view of the needle guide assembly of FIG. 6 taken along line 8—8.

DETAILED DESCRIPTION OF THE INVENTION

An assembly 10 for injecting a medicament within a patient is provided. The assembly is particularly well suited for performing pudendal and paracervical blocks during childbirth.

Figure 1:
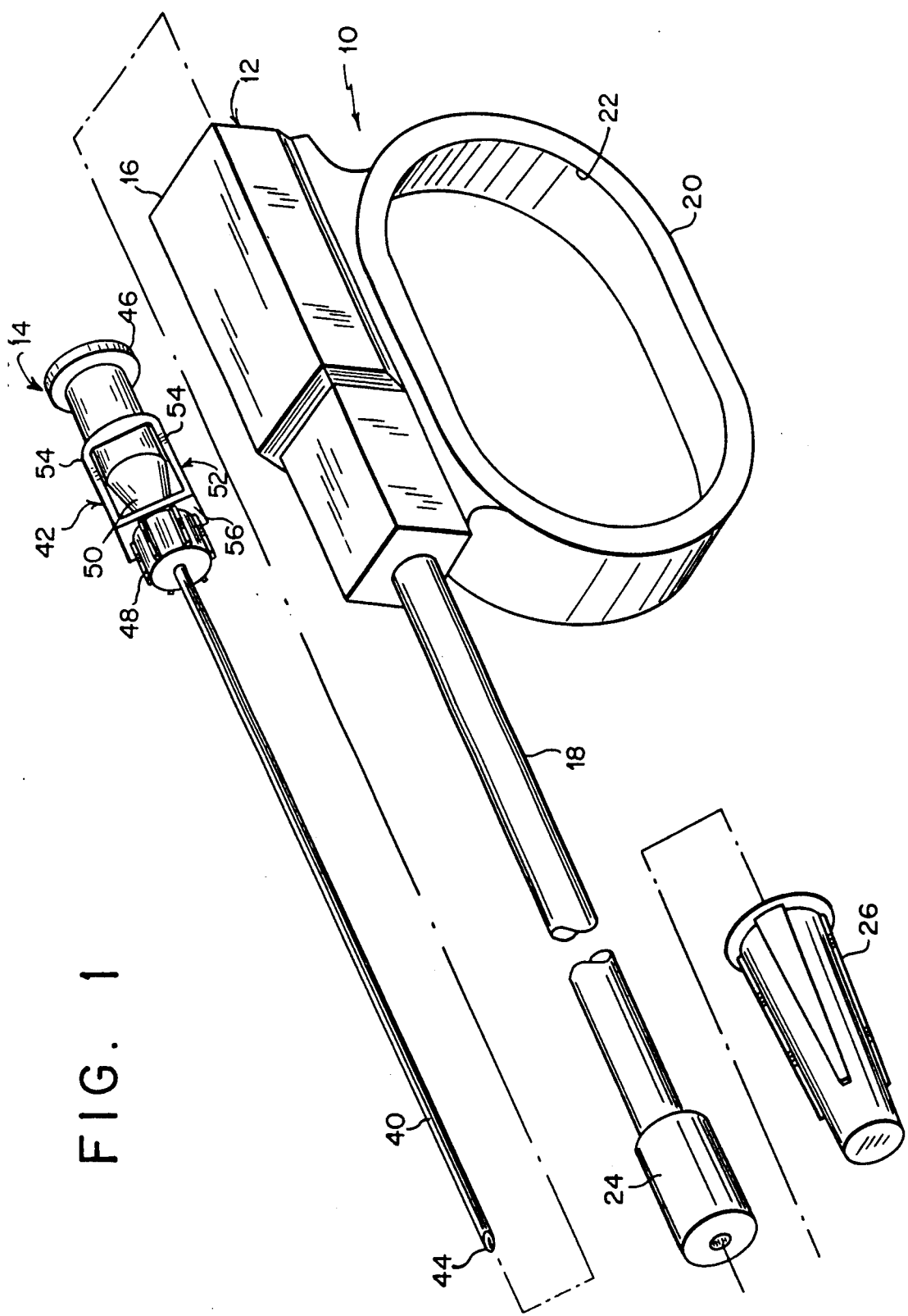
FIG. 1 is an exploded, perspective view of a pudendal/paracervical block needle assembly of the present invention.

Referring to FIG. 1, the assembly 10 includes a needle guide assembly 12 and a needle assembly 14. The needle guide assembly 12 includes a housing 16, a cannula 18 secured to the housing, and a handle 20 formed integrally with the housing. The handle 20 includes an oblong opening 22 to facilitate insertion of a thumb therein. A patient contacting collar 24 having a substantially blunt, rounded end is mounted to the distal end of the cannula.

As used herein, the term "distal" shall refer to components which are relatively near the patient and far from the person employing the assembly 10. "Proximal" refers to components which are relatively near the person employing the assembly. The collar allows the needle guide assembly 12 to be properly positioned within a body cavity without risk of injury to the patient. A protective cap 26 is mounted to the collar to protect against accidental punctures when the needle assembly 14 is inserted within the needle guide assembly 12.

Referring to FIGS. 2, 3, 6 and 8, the housing 16 includes a passage 28 extending therethrough. The passage includes three sections: a first cylindrical section 28A having a relatively small diameter, a second cylindrical section 28B having a larger diameter than the adjacent secton 28A, and a third section or recess 28C formed within the proximal end of the housing 16. The recess 28C is substantially square in cross section, and is defined by two pairs of substantialy parallel, opposing walls of substantially equal height.

The top and bottom walls 30,32 defining the recess each include integral steps 34 which function as an abutment as described below. The steps 34 may be in the form of ridges or any other projections which serve the purpose for which they are intended.

A second pair of opposing steps 36 are defined where the relatively large cylindrical section 28B of the passage adjoins the square section 28C thereof. The diameter of the middle section 28B is substantially the same as the distance between the steps 34. It is accordingly smaller than the distance between the two opposing side walls defining the sides of the recess 28C. The steps 36 are therefore defined at this juncture.

Figure 2:
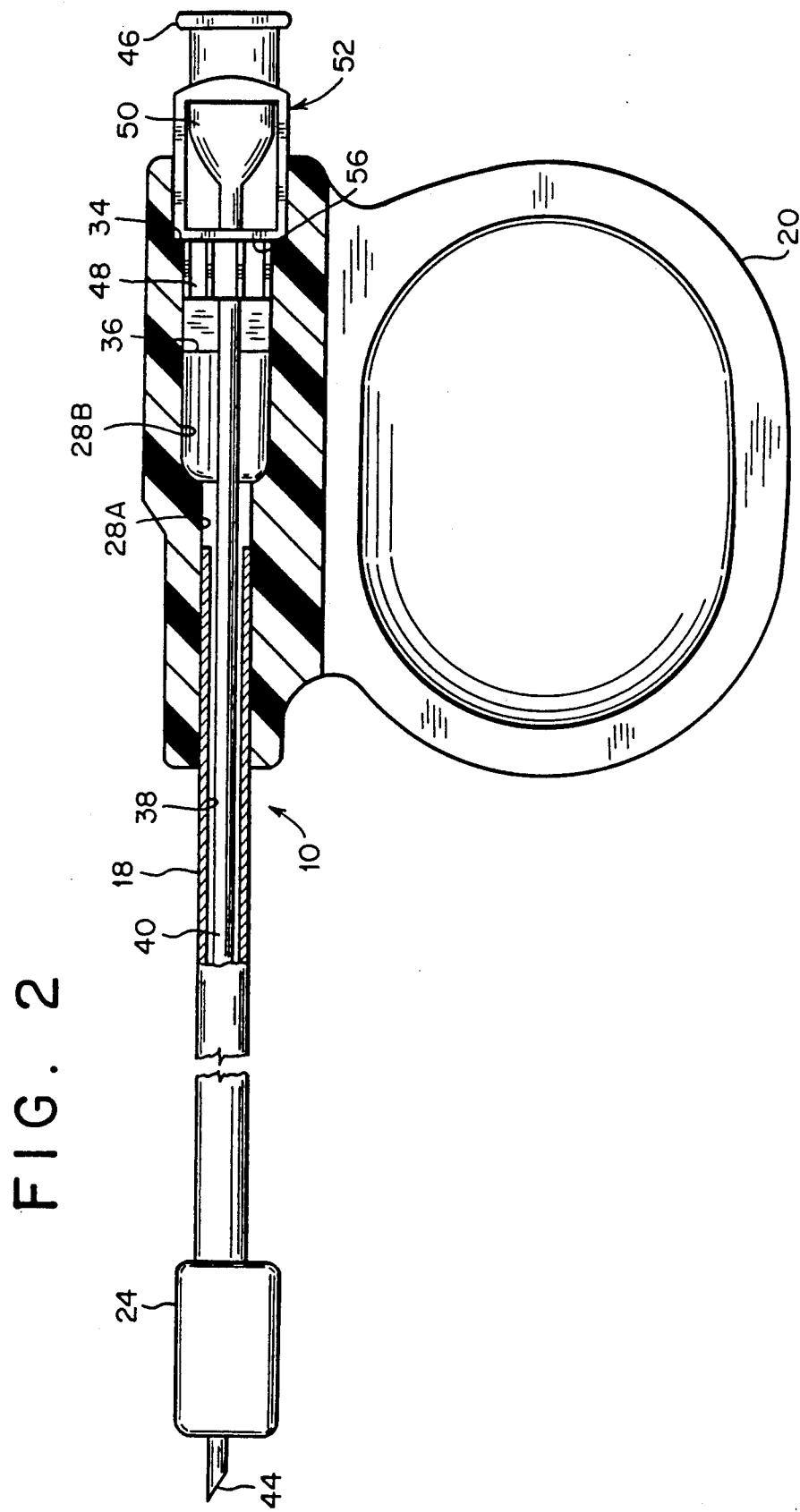
FIG. 2 is a partially cross-sectional side elevation view thereof showing a needle assembly in a first position with respect to a needle guide assembly.
Figure 3:
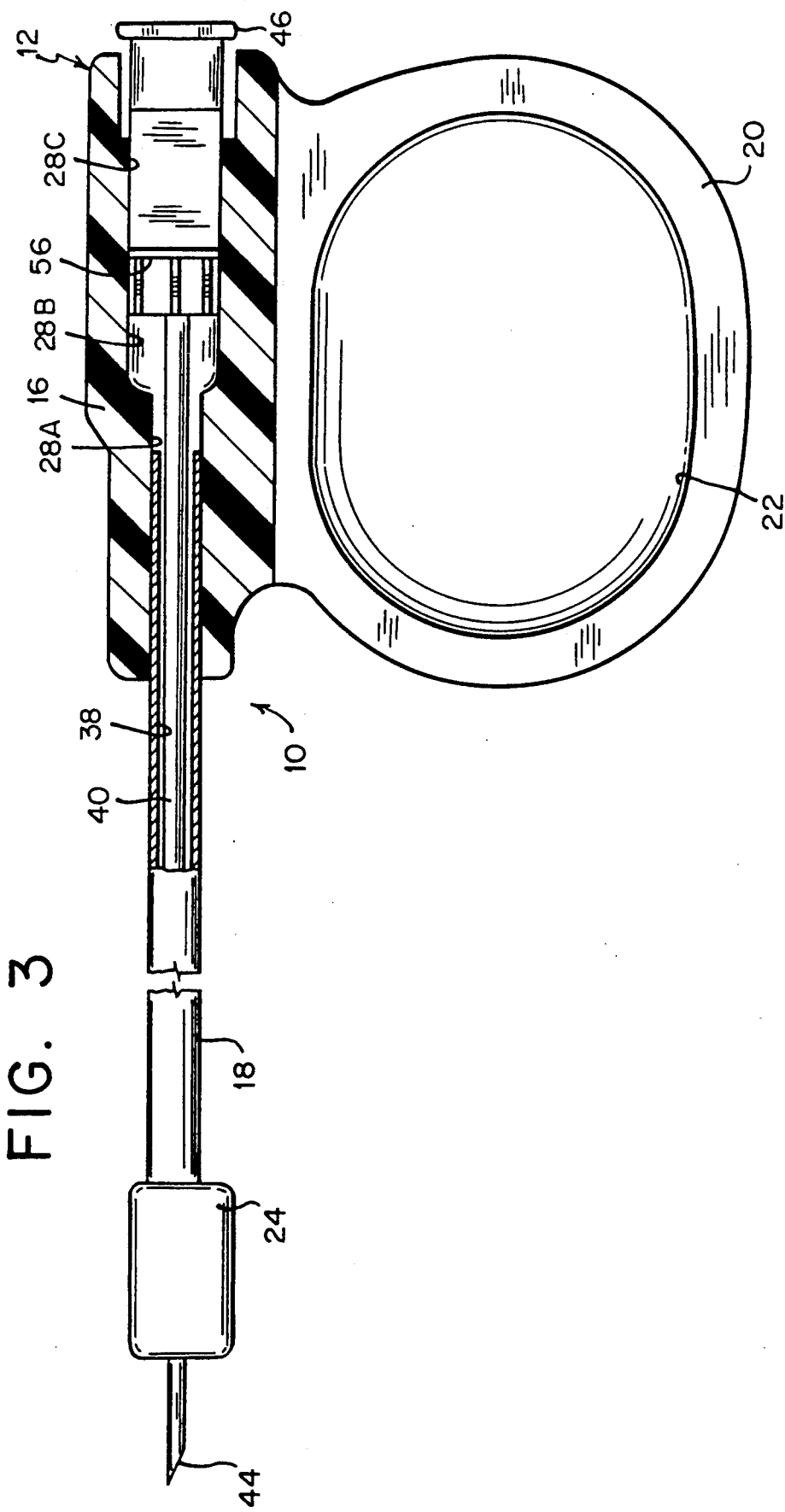
FIG. 3 is a similar view of the assembly of FIG. 2 showing the needle assembly in a second position with respect to the needle guide assembly.

As shown in FIGS. 2-3, the cannula 18 includes a lumen 38 which is in fluid communication with the passage 28 and is substantially coaxial therewith. The cannula may be made from stainless steel, while the housing can be molded from any suitable polymeric material. The distal end of the cannula is blunt, and is substantially coplanar with the distal end of the collar 24. The outside diameter of the cannula is substantially the same as the diameter of the distal section 28A of the passage 28 through the housing 16. The proximal end of the cannula 18 extends within this section 28A and is secured therein using adhesive or other suitable means.

The needle assembly 14 includes a stainless steel needle 40 or the like which is mounted to a plastic hub 42. The needle 40 has a beveled distal end 44.

The hub 42, as best shown in FIGS. 1, 4, 5 and 7 include a conduit extending therethrough. Hub 42 further comprises a cylindrical, proximal end portion 46 including a flanged end. The external configuration of the hub 42 and the geometry of the conduit formed therein facilitate its connection to a syringe (not shown) such as well known syringes having tapered luer tips or locking luer type tips.

The distal end portion 48 of the hub is also substantially cylindrical, and has a diameter slightly smaller than that of the middle section 28B of the needle guide assembly housing passage 28. A plurality of longitudinal ribs may be formed upon the outer surface of this end portion 48. The central portion of the hub includes a frustoconical housing 50 within a frame 52. The frustoconical housing is preferably transparent or translucent to allow the detection of a fluid such as blood therein. The proximal end of the needle 40 extends within this housing 50. The frame 52 includes a pair of opposing, parallel walls 54. The walls define a pair of flat surfaces 55 separated by a distance which is slightly smaller than the distance between the walls defining the needle guide housing recess 28C.

The distal end of the frame 52 includes an end wall 56 which defines a contact surface for engaging the first and second abutments defined by the steps 34, 36 extending within the recess 28C. The end wall 56 projects above and below the outer surface of the distal end portion 48 of the hub 42. The widths of the end wall 56 and frame 52 are substantially the same as the diameter of this distal end portion 48 of the hub. In other words, the maximum height of the frame as defined by the end wall 56 is substantially equal to the width of the recess 28C, and the maximum width of the frame is less than the distance between the steps 34 within the recess. The frame 52 accordingly has a generally rectangular outline when viewed in cross section through the end wall 56.

The assembly 10 described with reference to the figures is designed to allow two different depths of injection, namely five and ten millimeters. It will be appreciated that other depths or more than two depths may be provided. In order to provide a relatively deep injection, the needle assembly 14 is inserted within the needle guide assembly 12 as shown in FIG. 3. The rotational position of the needle assembly 14 is such that the larger dimension of the frame 52 is rotated ninety degrees with respect to the steps 34 within the housing 16. The hub 42, and particularly the end wall 56 thereof, do not engage the steps 34 as it is moved axially toward the distal end of the needle guide assembly 12. When the end wall 56 engages the second set of steps 36 distal to the relatively proximal steps 34, the needle tip 44 is about ten millimeters beyond the distal end of the collar 24. The distal end portion 48 of the hub is entirely within the middle section 28B of the passage 28 when the needle assembly 14 is in this position.

In order to move the needle assembly 14 to a position where the needle tip 44 extends only five millimeters beyond the end of the collar 24, it is withdrawn from the position shown in FIG. 3 until at least the frame 52 is located outside the recess 28C in the housing 16. The needle assembly is then rotated ninety degrees about its longitudinal axis and moved distally with respect to the needle guide assembly. The needle assembly can be moved axially until the end wall 56 of the hub frame 52 engages the relatively proximal steps 34, as shown in FIG. 2. Since the two sets of steps 34, 36 are five millimeters apart, the needle 40 extending through the cannula 18 projects only five millimeters therefrom.

The respective geometries of the needle hub 42 and recess 28C provide a positive locking mechanism which prevents the needle 40 from rotating in either direction when an injection is made. This is an important feature of the present invention. The present invention also provides an assembly capable of two or more depths of needle penetration beyond its collar. Changing the depth of penetration can be accomplished without removing the needle from the cannula, and without the use of separate removable spacer elements. This, also, is an important feature of the present invention. The incorporation of a translucent or transparent needle hub allows the user to detect blood very quickly should a blood vessel be accidentally punctured.

The assembly 10 is particularly well adapted for providing pudendal and/or paracervical blocks, and may be incorporated into a procedural tray for sterile, single use. When labor is definitely established and the cervix is dilated about four centimeters, the needle guide is positioned adjacent the pudendal nerve and a puncture is made. The site of penetration is aspirated using a hand controlled syringe filled with the desired amount of anesthetic solution. If blood is obtained, the entire assembly is withdrawn and the injection site in question temporarily abandoned until the other injection site or sites are completed. If no blood is detected, the injection may be completed.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An assembly for injecting a medicament within a body, comprising:
    a needle guide assembly, said needle guide assembly including a housing, said housing including first and second end portions;
    a recess defined within said first end portion of said housing;
    first abutment means projecting from said housing and into said recess;
    second abutment means defined by said housing providing a discrete step without threads from first abutment;
    a cannula secured to said second end portion of said housing, said cannula including an elongate lumen and having a distal end, said lumen being in fluid communication with said recess;
    a needle assembly, said needle assembly including a hub and a needle secured to said hub, said needle and said hub being insertable within said lumen and said recess, respectively;
    said hub being configured such that said hub engages said first abutment means when inserted within said recess in a first rotational position, and engages said second abutment means when inserted within said recess in a second rotational position, said needle projecting a first distance beyond said distal end of said cannula when said hub engages said first abutment means and a second distance beyond said distal end of said cannula when said hub engages said second abutment means.

2. An assembly as defined in claim 1 wherein said first abutment means is a step defined by a wall of said housing.

3. An assembly as defined in claim 1 wherein said recess is defined by a first pair of opposing, substantially parallel walls and a second pair of opposing, substantially parallel walls, said second pair of walls respectively connecting said first pair of walls.

4. An assembly as defined in claim 3 wherein said first pair of walls are separated from each other by substantially the same distance separating said second pair of walls.

5. An assembly as defined in claim 4 wherein said first abutment means includes a first step defined by at least one of said walls.

6. An assembly as defined in claim 3 wherein said first abutment means includes a pair of steps in opposing relation to each other, said steps projecting, respectively from one of said first or second pairs of opposing walls.

7. An assembly as defined in claim 5 wherein said hub includes a first contact surface, said first contact surface being positioned so as to contact said first step when said hub is inserted within said recess while in said first rotational position, said first contact surface being positioned to avoid contacting said first step when said hub is inserted within said recess while in said second rotational position.

8. An assembly as defined in claim 5 wherein said first step is located nearer to said first end portion of said housing and farther from said distal end of said cannula than said second abutment means.

9. An assembly as defined in claim 8 wherein said second abutment means includes a second step defined by one of said walls, said second step forming a substantially perpendicular angle with respect to said first step.

10. An assembly as defined in claim 1 wherein said first abutment means is located nearer than said second abutment means to said first end portion of said housing.

11. An assembly as defined in claim 10 wherein said first abutment means includes a pair of opposing steps extending within said recess from said housing.

12. An assembly as defined in claim 11 wherein said second abutment means includes a pair of opposing steps extending within said recess from said housing.

13. An assembly as defined in claim 12 wherein said first end portion of said housing includes four adjoining, substantially perpendicular walls, said four substantially perpendicular walls being substantially equal in height, at least a first portion of said recess being defined by said four substantially perpendicular walls.

14. An assembly as defined in claim 13 wherein said hub includes a distal end portion insertable within said recess, said distal end portion of said hub having a maximum height grater than the maximum width of said distal end portion of said hub.

15. An assembly as defined in claim 14 wherein said recess includes a cylindrical portion extending from said first portion thereof, and said hub includes a cylindrical end insertable within said cylindrical portion of said recess.

16. An assembly as defined in claim 14 wherein said hub includes a proximal end portion, said proximal end portion of said hub extending outside of said recess when said hub engages either said first abutment means or said second abutment means.

17. An assembly as defined in claim 1 wherein said hub includes a proximal end portion in fluid communication with said needle, said proximal end portion of said hub extending outside of said recess when said hub engages either said first abutment means or said second abutment means.

18. An assembly as defined in claim 1 including a handle extending from said housing, said handle including an oblong opening.

19. An assembly as defined in claim 1 including a collar mounted to said distal end of said cannula.

20. An assembly for injecting a medicament within a body, comprising:
    a needle guide assembly, said needle guide assembly including a housing and a passage extending through said housing;
    abutment means extending within said passage from said housing;
    a cannula secured to said housing, said cannula including a lumen in fluid communication with said passage;

a needle assembly, said needle assembly including a hub and a needle secured to said hub, said needle and said hub being insertable within said lumen and said passage, respectively;

said hub including a first end portion for insertion within said passage and a second end portion, said first end portion including a maximum height greater than the maximum width of said first end portion of said hub, whereby said first end portion of said hub will engage said abutment means when inserted within said passage in a first rotational orientation, but will avoid engaging said abutment means when inserted within said passage in a second rotational orientation, said hub being insertable to a greater depth within said passage when in said second rotational orientation than when in said first rotational orientation.

21. An assembly as defined in claim 20 wherein said passage includes a section which is substantially square in cross section, and said first end portion of said hub includes a substantially rectangular cross section throughout at least part of its length.

22. An assembly as defined in claim 20 including a handle extending from said housing, said handle including an oblong opening.

23. An assembly as defined in claim 20 wherein said hub includes a conduit extending therethrough, said conduit being visible through said hub.

24. An assembly as defined in claim 20 including second abutment means extending within said passage from said housing.

25. An assembly as defined in claim 24 wherein each of said abutment means includes a pair of opposing steps.

26. An assembly as defined in claim 25 wherein one of said paris of opposing steps is located distally with respect to the other pair of opposing steps.

27. An assembly as defined in claim 20 wherein said cannula includes a proximal end secured to said housing and a distal end, and including a collar mounted to said distal end of said cannula.

* * * * *